United States Patent
Miyakura (10) Patent No.: US 9,111,332 B2
(45) Date of Patent: Aug. 18, 2015

(54) METHOD AND APPARATUS FOR HARDNESS TESTER

(71) Applicant: MITUTOYO CORPORATION, Kanagawa (JP)

(72) Inventor: Jyota Miyakura, Chiba (JP)

(73) Assignee: MITUTOYO CORPORATION, Kanagawa (JP)

( * ) Notice: Subject to any disclaimer, the term of this patent is extended or adjusted under 35 U.S.C. 154(b) by 0 days.

(21) Appl. No.: 14/219,192

(22) Filed: Mar. 19, 2014

(65) Prior Publication Data

US 2014/0294282 A1 Oct. 2, 2014

(30) Foreign Application Priority Data

Mar. 28, 2013 (JP) ................. 2013-067828

(51) Int. Cl.
| | | |
|---|---|---|
| G06K 9/36 | (2006.01) | |
| G06T 7/00 | (2006.01) | |
| G01N 3/06 | (2006.01) | |
| G01N 3/42 | (2006.01) | |
| G06K 9/62 | (2006.01) | |

(52) U.S. Cl.
CPC ............... *G06T 7/001* (2013.01); *G01N 3/068* (2013.01); *G01N 3/42* (2013.01); *G06K 9/6203* (2013.01); *G01N 2203/008* (2013.01); *G01N 2203/0019* (2013.01); *G01N 2203/0647* (2013.01)

(58) Field of Classification Search
None
See application file for complete search history.

(56) References Cited

U.S. PATENT DOCUMENTS

2014/0078299 A1   3/2014   Kataoka

FOREIGN PATENT DOCUMENTS

JP          4029832 B2     1/2008

OTHER PUBLICATIONS

Gadermayr et al., "Robust algorithm for automated microindentation measurement in Vickers hardness testing", Journal of Electronic Imaging 21(2), 021109 (Apr.-Jun. 2012), cover page + pp. 021109-1 through 021109-12 (13 total pages).*

Andreas Maier et al., "Robust Automatic Indentation Localisation and Size Approximation for Vickers Microindentation Hardness Indentations", 7th International Symposium on Image and Signal Processing and Analysis (ISPA 2011), Sep. 4-6, 2011, Dubrovnik, Croatia, pp. 295-300.*

* cited by examiner

*Primary Examiner* — Brian P Werner
(74) *Attorney, Agent, or Firm* — Greenblum & Bernstein, P.L.C.

(57) ABSTRACT

A hardness tester has an indentation former forming an indentation by pressing an indenter against a surface of a sample; an image capture controller controlling a CCD camera to capture an image of the surface of the sample and obtain image data; an indentation area extractor extracting an indentation area based on the obtained image data; and a hardness calculator calculating hardness of the sample based on the extracted indentation area. The indentation area extractor has a reduced image generator reducing the image obtained from the image data of the surface of the sample at a scale ratio selected from a plurality of predetermined scale ratios and generating a reduced image; and a pattern matcher performing pattern matching with respect to the generated reduced image and extracting the indentation area.

18 Claims, 11 Drawing Sheets

METHOD AND APPARATUS FOR HARDNESS TESTER

CROSS-REFERENCE TO RELATED APPLICATIONS

The present application claims priority under 35 U.S.C. §119 of Japanese Application No. 2013-067828 filed on Mar. 28, 2013, the disclosure of which is expressly incorporated by reference herein in its entirety.

BACKGROUND OF THE INVENTION

1. Field of the Invention

The present invention relates to a hardness tester and a method of testing hardness.

2. Description of Related Art

A conventionally known hardness tester measures hardness of a sample based on dimensions of an indentation formed by pressing an indenter against the sample with a predetermined test force. For example, a Vickers hardness tester presses a quadrangular pyramidal indenter into a surface of a sample and measures a length of a diagonal line of a formed indentation. The Vickers hardness tester calculates hardness based on the measured length of the diagonal line of the indentation.

In testing hardness of a metal material, a known hardness tester generally executes binarization by determining whether a luminance value is below a predetermined value (threshold value) with respect to an image of a surface of a sample captured by an image capturer, and then extracts an indentation area formed in the surface of the sample (refer to Japanese Patent No. 4029832, for example).

Figure 14:
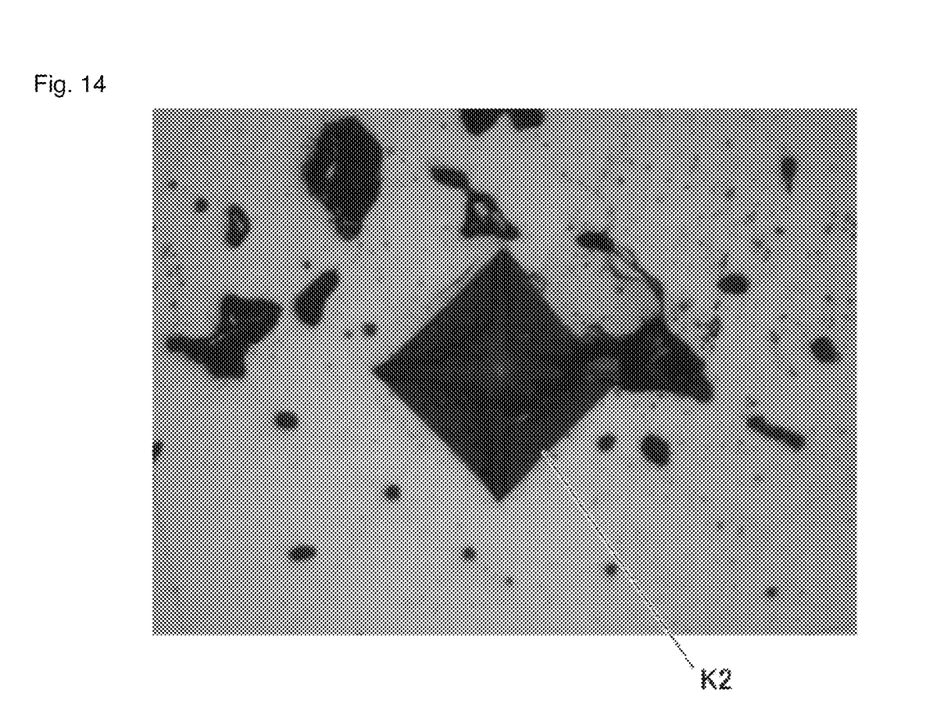
FIG. 14 illustrates an example in which the vicinity of a formed indentation is contaminated.

In the conventional hardness tester above, however, a change in luminance, such as shading, occurs throughout the captured image. Thus, the conventional hardness tester is sometimes unable to extract the indentation area accurately due to an impact of the change in luminance during binarization of the entire image. In the case of a small indentation area in particular, accurate extraction of the indentation area is difficult. In addition, the conventional hardness tester has difficulty extracting an indentation area accurately in a case where the vicinity of a formed indentation K2 is contaminated as shown in FIG. 14.

SUMMARY OF THE INVENTION

A non-limiting feature of the disclosure provides a hardness tester and a method of testing hardness that enable accurate extraction of an indentation area.

In view of the above, a first aspect of the present disclosure provides a hardness tester measuring hardness of a sample by applying a predetermined test force to a surface of the sample with an indenter to form an indentation and measuring dimensions of the indentation. The hardness tester includes an indentation former forming the indentation in the surface of the sample by pressing the indenter against the surface of the sample; an image capture controller controlling an image capturer to capture an image of the surface of the sample and to obtain image data of the surface of the sample; an indentation area extractor extracting an indentation area formed in the surface of the sample based on the image data of the surface of the sample obtained by the image capture controller; and a hardness calculator calculating the hardness of the sample based on the indentation area extracted by the indentation area extractor. The indentation area extractor includes a reduced image generator reducing the image obtained from the image data of the surface of the sample at a scale ratio selected from a plurality of predetermined scale ratios and generating a reduced image: and a pattern matcher performing pattern matching with respect to the reduced image generated by the reduced image generator and extracting the indentation area.

A second aspect of the present disclosure provides the hardness tester according to the first aspect, in which the pattern matcher extracts the indentation area based on a degree of correlation calculated by scanning the reduced image with a model including an indentation shape corresponding to the indenter.

A third aspect of the present disclosure provides the hardness tester according to the second aspect, in which the pattern matcher calculates the degrees of correlation by scanning the reduced image at the scale ratios in a predetermined sequence. When a maximum degree of correlation among the calculated degrees of correlation is determined to be equal to or greater than a predetermined threshold value, the pattern matcher extracts an area showing the maximum degree of correlation as the indentation area.

A fourth aspect of the present disclosure provides the hardness tester according to the second or third aspect, in which the pattern matcher extracts, as the indentation area, the area showing the maximum degree of correlation among all degrees of correlation calculated by scanning all reduced images at all scale ratios.

A fifth aspect of the present disclosure provides the hardness tester according to one of the first to fourth aspects, further including a display controller displaying on a display the hardness of the sample calculated by the hardness calculator.

A sixth aspect of the present disclosure provides a method of testing hardness with a hardness tester by applying a predetermined test force to a surface of a sample with an indenter to form an indentation and measuring dimensions of the indentation. The method includes indentation forming to form the indentation in the surface of the sample by pressing the indenter against the surface of the sample; image capture control to control an image capturer to capture an image of the surface of the sample and obtain image data of the surface of the sample; indentation area extraction to extract an indentation area formed in the surface of the sample based on the image data of the surface of the sample obtained in the image capture control; and hardness calculation to calculate the hardness of the sample based on the indentation area extracted in the indentation area extraction. The indentation area extraction includes reduced image generation to reduce the image obtained from the image data of the surface of the sample at a scale ratio selected from a plurality of predetermined scale ratios and generate a reduced image; and pattern matching to perform pattern matching with respect to the reduced image generated in the reduced image generation and extract the indentation area.

According to the present disclosure, it is unnecessary to perform binarization to extract the indentation area, thus enabling accurate extraction of the indentation area without being affected by a change in luminance or a contamination.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF PREFERRED EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description is taken with the drawings making apparent to those skilled in the art how the forms of the present invention may be embodied in practice.

Figure 1:
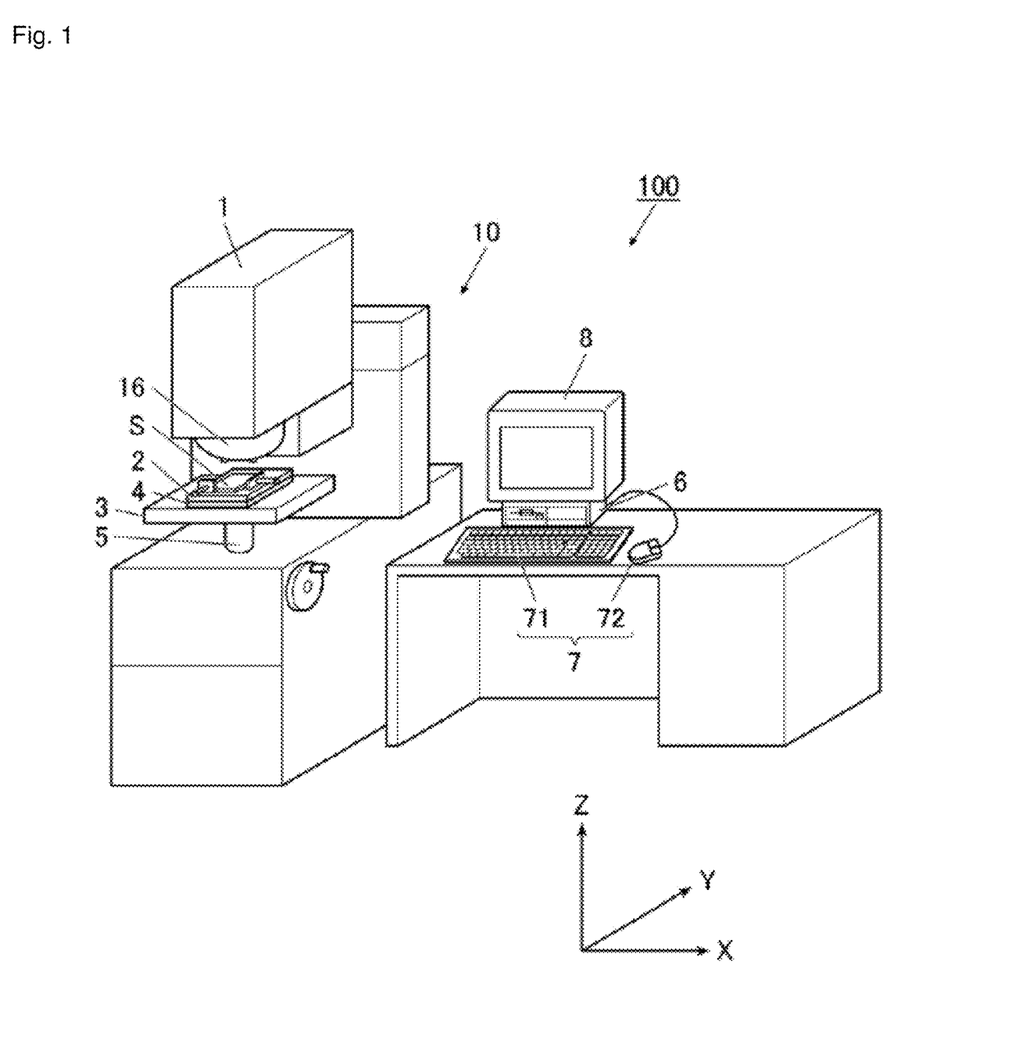
FIG. 1 is a perspective view of an overall configuration of a hardness tester according to the present invention.

An embodiment of the present disclosure is described below in detail with reference to the drawings. In the description below, an X direction is a left-right direction, a Y direction is a front-back direction, and a Z direction is an up-down direction in FIG. 1. Furthermore, an X-Y plane is a horizontal plane.

A hardness tester 100 is a Vickers hardness tester, for example, that includes an indenter 14a (see FIG. 3) having a square planar shape. With reference to FIGS. 1 to 4, the hardness tester 100 has a tester main body 10, a controller 6, an operator 7, and a monitor 8.

Figure 2:
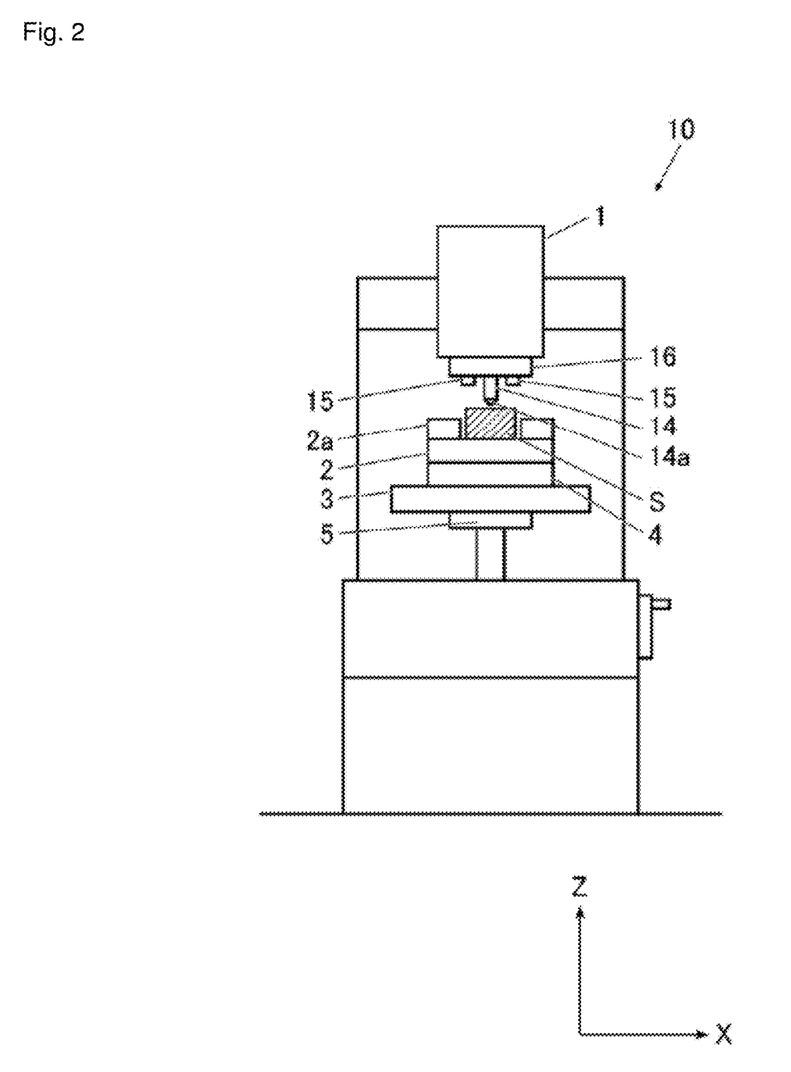
FIG. 2 is a schematic view of a hardness tester main body of the hardness tester according to the present invention.

With reference to FIG. 2, the tester main body 10 includes a hardness measurer 1 measuring hardness of a sample S; a sample stage 2 on which the sample S is placed; an XY stage 3 displacing the sample stage 2; an AF stage 4 for focusing on a surface of the sample S; and a lift mechanism 5 raising and lowering the sample stage 2 (the XY stage 3 and the AF stage 4).

Figure 3:
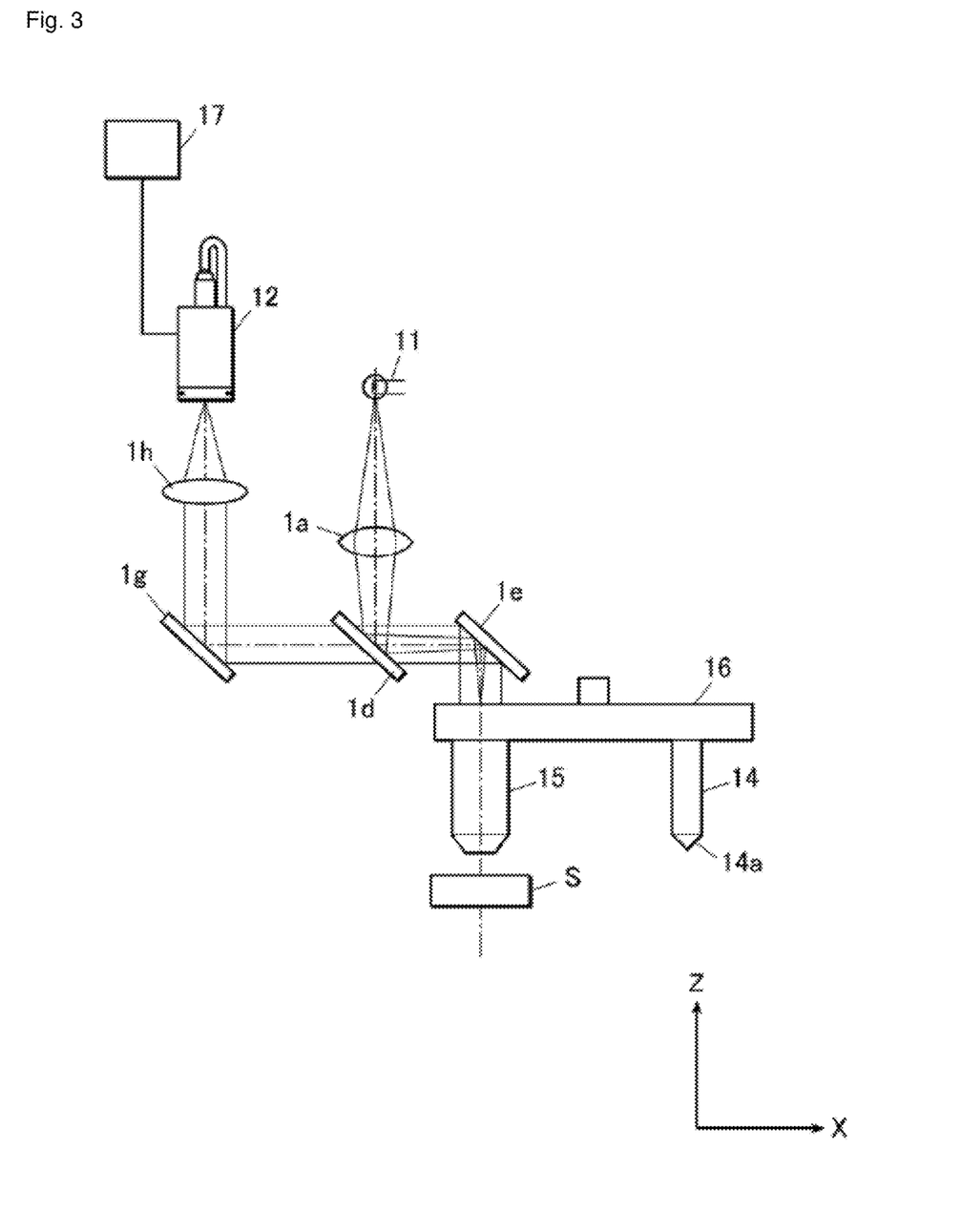
FIG. 3 is a schematic view of a hardness measurer of the hardness tester according to the present invention.

With reference to FIG. 3, the hardness measurer 1 includes an illuminating device 11 illuminating the surface of the sample S; a CCD camera 12 capturing an image of the surface of the sample S; and a turret 16. The turret 16 includes an indenter column 14, which includes the indenter 14a, and a field lens 15. The turret 16 is capable of switching between the indenter column 14 and the field lens 15 by rotating.

The illuminating device 11 emits light to illuminate the surface of the sample S. The light emitted from the illuminating device 11 reaches the surface of the sample S via a lens 1a, a half mirror 1d, a mirror 1e, and the field lens 15.

Based on reflected light input from the surface of the sample S via the field lens 15, the mirror 1e, the half mirror 1d, a mirror 1g, and a lens 1h, the CCD camera 12 obtains image data by capturing an image of the surface of the sample S as well as an indentation formed in the surface of the sample S by the indenter 14a. The CCD camera 12 then outputs the obtained image data to the controller 6 via a frame grabber 17, which is capable of simultaneously accumulating and storing a plurality of frames of image data. Thus, the CCD camera 12 serves as an image capturer in the present invention.

The indenter column 14 is displaced toward the sample S placed on the sample stage 2 by a load mechanism (not shown in the drawings), which is driven in response to a control signal output by the controller 6. The indenter 14a, provided on a forefront end of the indenter column 14, is pressed against the surface of the sample S with a predetermined test force. In the present embodiment, a quadrangular pyramidal Vickers indenter (with opposing angles of 136±0.5°) is used as the indenter 14a.

The field lens 15 is a collective lens, each lens having a different magnification. A plurality of the field lenses 15 are retained on a lower surface of the turret 16. The field lenses 15 are positioned above the sample S by rotating the turret 16. Thereby, the light emitted from the illuminating device 11 uniformly illuminates the surface of the sample S.

The turret 16 is configured so as to enable the indenter column 14 and the plurality of field lenses 15 to be attached to the lower surface thereof. The turret 16 is also configured to be capable of positioning any one of the indenter column 14 and the plurality of field lenses 15 above the sample S by rotating the turret 16 around a Z-axis direction. Specifically, the indentation can be formed in the surface of the sample S by positioning the indenter column 14 above the sample S while the formed indentation can be observed by positioning the field lenses 15 above the sample S.

The sample S is placed on an upper surface of the sample stage 2 and is fixed in place with a sample holder 2a. The XY stage 3 is driven by a drive mechanism (not shown in the drawings) driven in response to the control signal output by the controller 6. The XY stage 3 then displaces the sample stage 2 in a direction (X and Y directions) perpendicular to the displacement direction (Z direction) of the indenter 14a. The AF stage 4 is driven in response to the control signal output by the controller 6. The AF stage 4 then minutely raises and lowers the sample stage 2 based on the image data captured by the CCD camera 12 to locus on the surface of the sample S. The lift mechanism 5 is driven in response to the control signal output by the controller 6. The lift mechanism 5 then displaces the sample stage 2 (the XY stage 3 and the AF stage 4) in the Z direction to change a relative distance between the sample stage 2 and the field lenses 15.

The operator 7 has a keyboard 71 and a mouse 72. The operator 7 receives an operation input by a user when carrying out a hardness test. Upon receiving a predetermined input operation from the user, the operator 7 generates a predetermined operation signal associated with the input operation and outputs the operation signal to the controller 6. Specifically, the operator 7 receives an operation in which the user selects a condition to determine a focus position of the indentation. The operator 7 also receives an operation in which the user designates a range of displacement (a range of relative distance between the sample stage 2 and the field lenses 15) of the sample stage 2 (the lift mechanism 5 and the AF stage 4). In addition, the operator 7 receives an operation in which the user enters a test condition value when carrying out the hardness test with the hardness tester 100. The entered test condition value is transmitted to the controller 6. Herein, the test condition value is a value such as a material of the sample S, a test force (N) loaded on the sample S by the indenter 14a, or a magnification power of the field lenses 15, for example. In addition, the operator 7 receives an operation in which the user selects a manual mode, in which the focus position of the indentation is manually determined, or an automatic mode, in which the determination is made automatically. Furthermore, the operator 7 receives an operation in which the user programs a test position when carrying out the hardness test.

The monitor 8 is, for example, a display apparatus, such as an LCD. The monitor 8 displays settings of the hardness test input on the operator 7, results of the hardness test, and an image of the surface of the sample S and the indentation formed in the surface of the sample S captured by the CCD camera 12. Thus, the monitor 8 serves as a display in the present invention.

Figure 4:
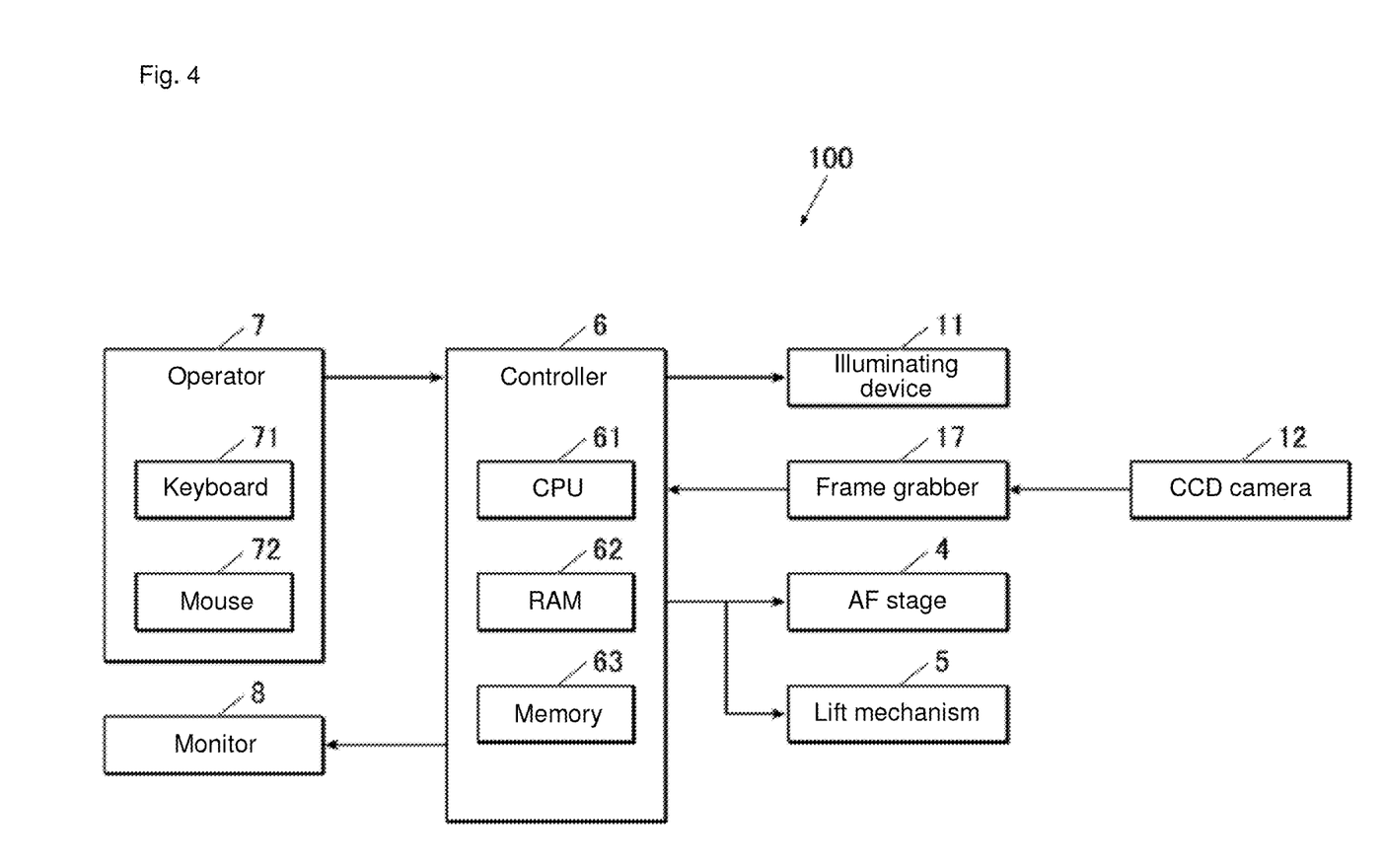
FIG. 4 is a block diagram of a control structure of the hardness tester according to the present invention.

As shown in FIG. 4, the controller 6 includes a CPU 61, a RAM 62, and a memory 63. The controller 6 controls an operation for performing a predetermined hardness test by executing a predetermined program stored in the memory 63.

The CPU 61 retrieves a processing program stored in the memory 63, then loads and executes the processing program in the RAM 62. The CPU 61 thus performs overall control of the hardness tester 100. The RAM 62 loads the processing program executed by the CPU 61 in a program storage area within the RAM 62 and stores, in a data storage area, input data and processing results generated during execution of the processing program, and the like. The memory 63 includes, for example, a recording medium (not shown in the drawing) storing a program, data, and the like. The recording medium includes a semiconductor memory and the like. The memory 63 stores various kinds of data, various kinds of processing programs, and data processed by running the programs, which allow the CPU 61 to perform overall control of the hardness tester 100. The memory 63 also stores in advance a plurality of scale ratios to reduce an image obtained from the image data of the surface of the sample S captured by the CCD camera 12. Furthermore, the memory 63 stores in advance a selection sequence of the plurality of scale ratios to reduce the image obtained from the image data of the surface of the sample S.

Figure 5:
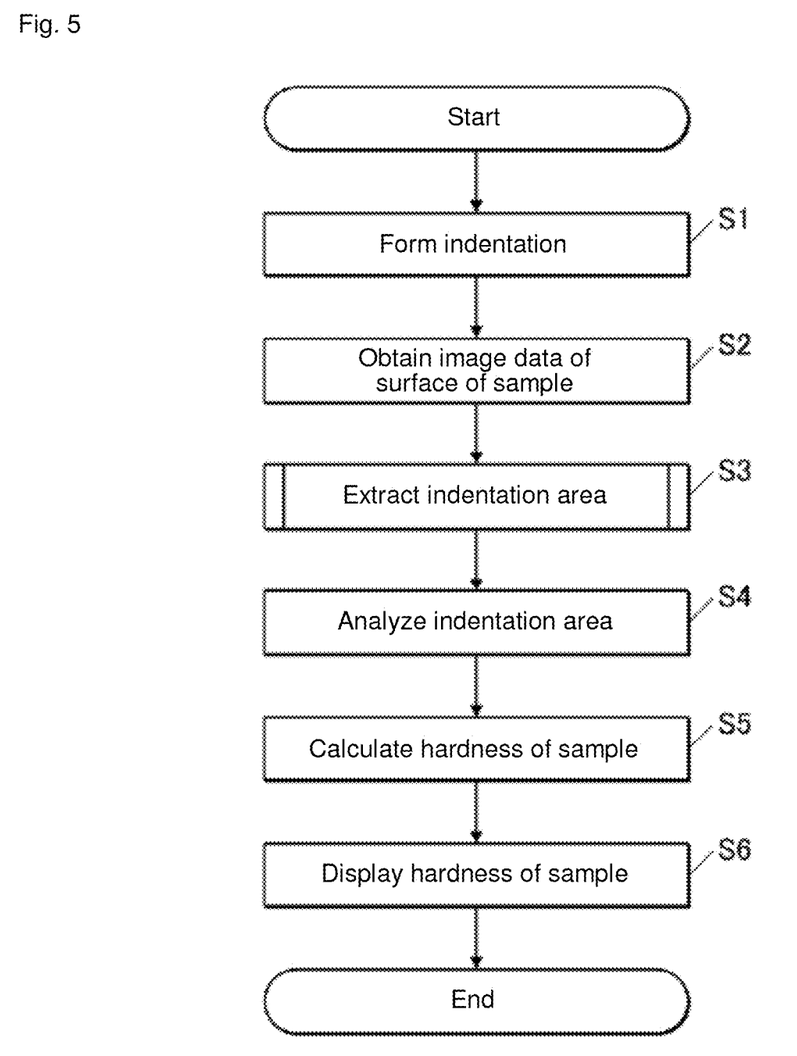
FIG. 5 is a flowchart of operations of the hardness tester according to the present invention.

Operations of the hardness tester 100 according to the present embodiment are described below with reference to a flowchart of FIG. 5. First, the indentation is formed in the surface of the sample S by the indenter 14a (Step S1: Indentation forming). Specifically, the user first places the sample S for the hardness test on the upper surface of the sample stage 2 and fixes the sample S in place with the sample holder 2a. Then, the CPU 61 rotates the turret 16 to position the indenter column 14 in a predetermined position opposite the sample S. The CPU 61 drives the load mechanism (not shown in the drawings) so as to lower the indenter column 14 to form the indentation in the surface of the sample S with the indenter 14a on the forefront end of the indenter column 14. Thus, the CPU 61 serves as an indentation former that forms the indentation in the surface of the sample S by pressing the indenter 14a against the surface of the sample S.

Figure 6:
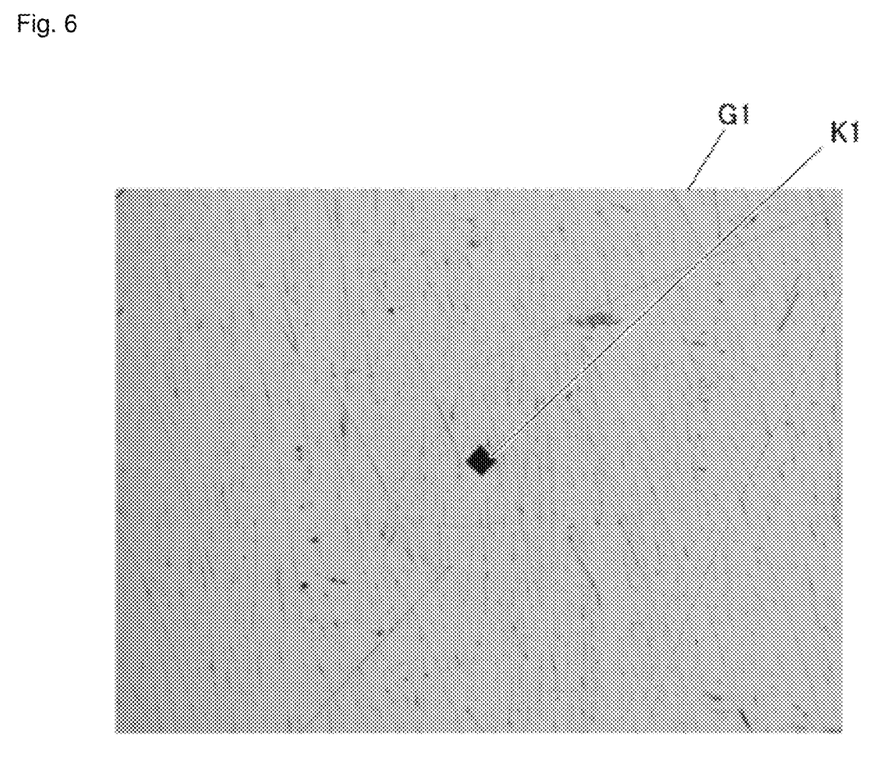
FIG. 6 illustrates an exemplary image obtained from image data of a surface of a sample.

Subsequently, image data for the surface of the sample S is obtained (Step S2: Image capture control). Specifically, the CPU 61 first rotates the turret 16 to position the field lenses 15, instead of the indenter column 14, in a predetermined position opposite the sample S. The CPU 61 then raises and lowers the lift mechanism 5 and the AF stage 4 based on image data captured by the CCD camera 12 through the field lenses 15 so as to focus on the surface of the sample S. The CPU 61 causes the CCD camera 12 to capture an image of the surface of the sample S and obtain the image data of the surface of the sample S. Thus, the CPU 61 serves as an image capture controller that controls the CCD camera 12 to capture the image of the surface of the sample S and obtain the image data of the surface of the sample S. FIG. 6 illustrates an exemplary image G1 obtained from image data of the surface of the sample S captured in Step S2. In FIG. 6, K1 represents an indentation area formed in the surface of the sample S.

Subsequently, the indentation area is extracted (Step S3: Indentation area extraction). Specifically, the CPU 61 extracts the indentation area K1 formed in the surface of the sample S based on the image data of the surface of the sample S obtained in Step S2. Thus, the CPU 61 serves as an indentation area extractor that extracts the indentation area K1 formed in the surface of the sample S based on the image data of the surface of the sample S obtained by the image capture controller.

Figure 7:
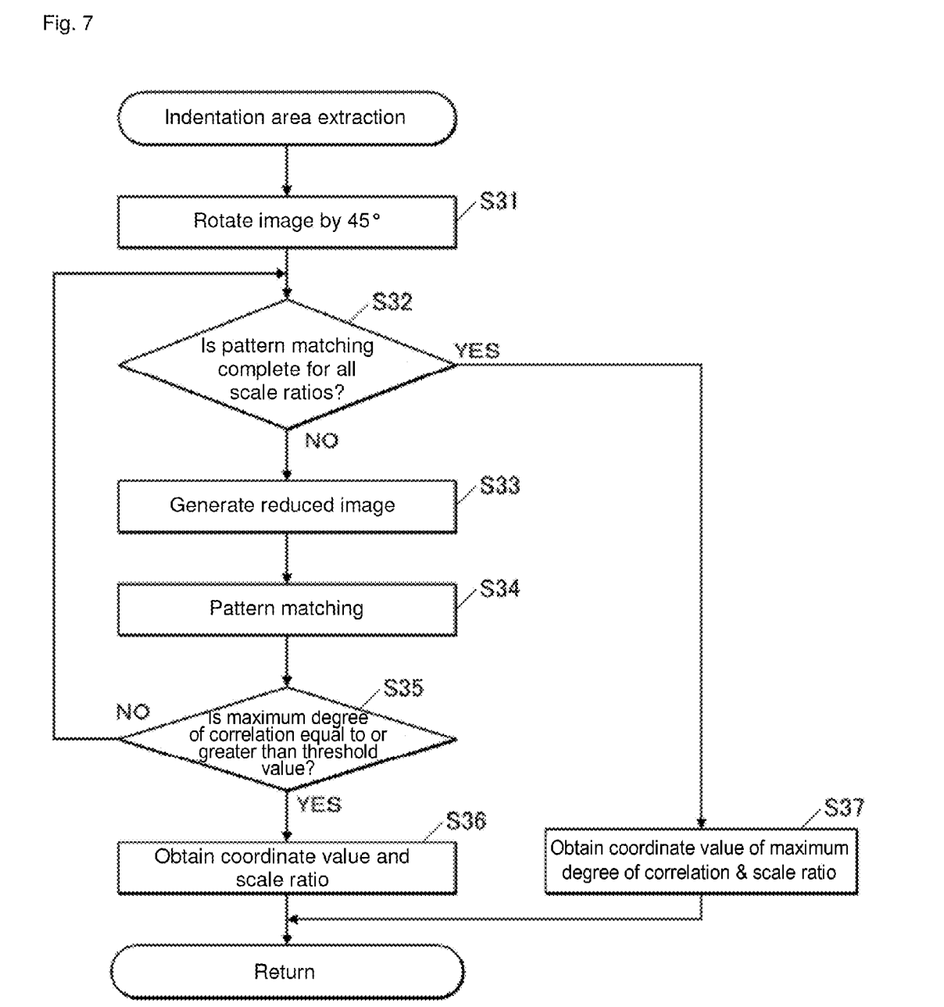
FIG. 7 is a flowchart of indentation area extraction in the hardness tester according to the present invention.
Figure 8:
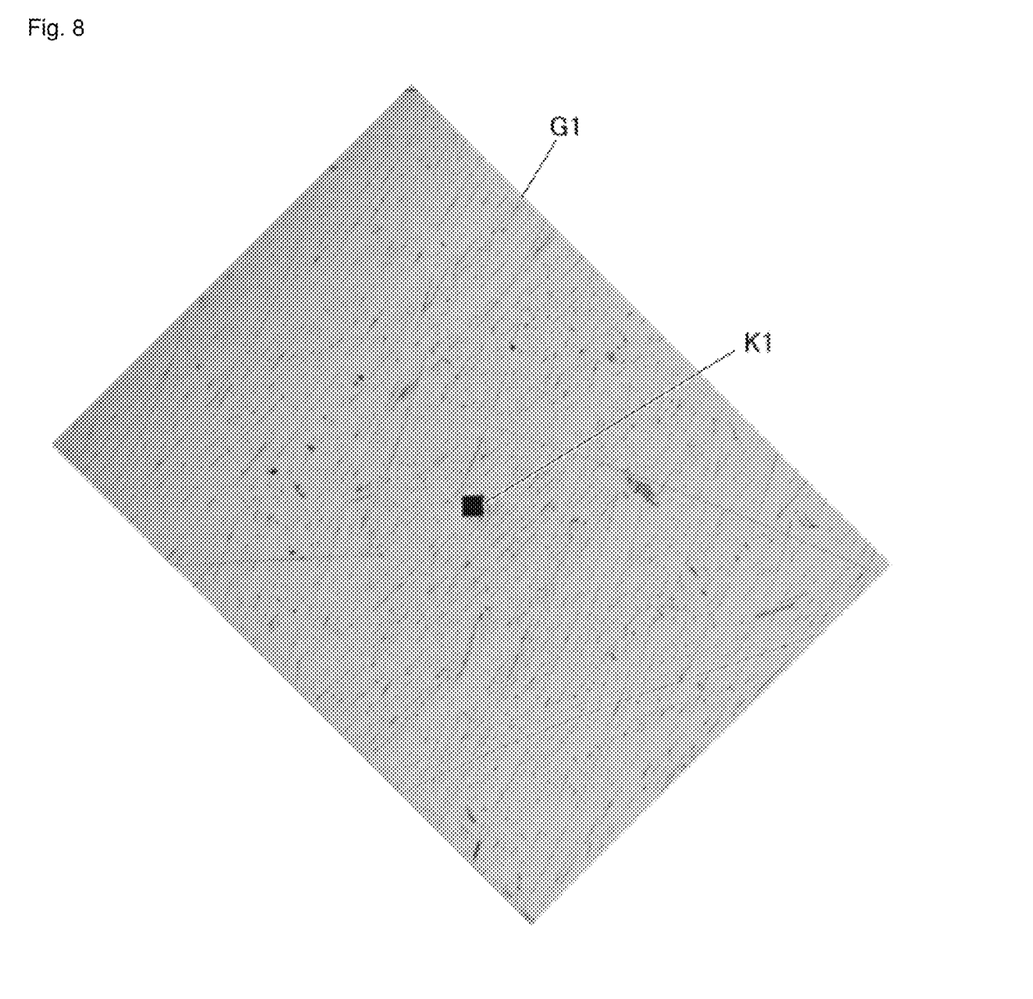
FIG. 8 is a view of the image of FIG. 6 rotated by 45°.

More specifically, the image G1 is first rotated by 45° as shown in a flowchart of FIG. 7 (Step S31). Specifically, with reference to FIG. 8, the CPU 61 rotates by 45° the image G1 (refer to FIG. 6) obtained in Step S2 of FIG. 5.

Then, a determination is made as to whether pattern matching is complete for all scale ratios (Step S32). Specifically, the CPU 61 determines whether the pattern matching (refer to Step S34) is complete with respect to all scaled-down images of the image G1, which is rotated by 45° in Step S31, at all scale ratios stored in the memory 63. When the pattern matching is determined to be complete for all scale ratios (Step S32: Yes), the CPU 61 proceeds to Step S37. When the pattern matching is determined not to be complete for at least one scale ratio (Step S32: No), the CPU 61 proceeds to Step S33.

Figure 9:
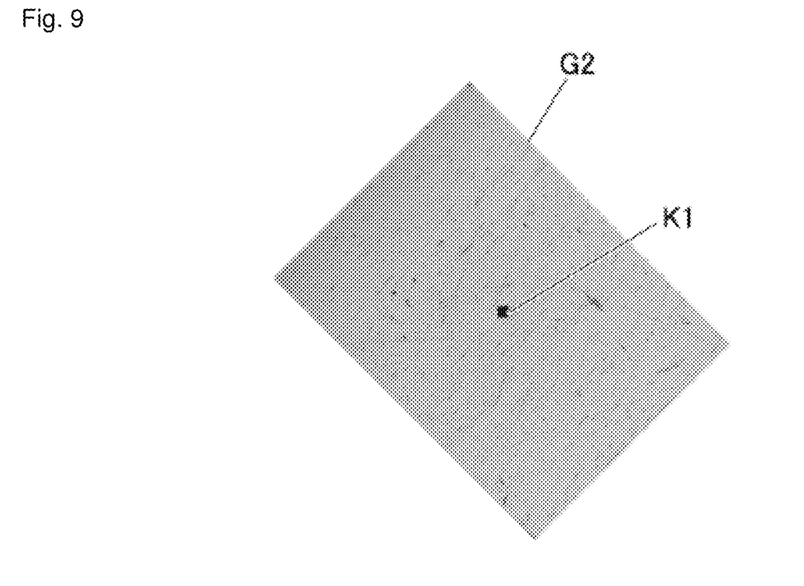
FIG. 9 illustrates an exemplary reduced image of FIG. 8.

Then, a reduced image is generated (Step S33: Reduced image generation). Specifically, the CPU 61 reduces the image G1, which is rotated by 45° in Step S31, at a scale ratio selected from the plurality of scale ratios stored in the memory 63 and generates a reduced image G2. FIG. 9 illustrates an exemplary reduced image G2 generated in Step S33. The reduced image G2 generated in Step S33 is an image reduced at a scale ratio for which the pattern matching has not been completed. Thus, the CPU 61 serves as a reduced image generator that reduces the image G1 obtained from the image data of the surface of the sample S at the scale ratio selected from the plurality of predetermined scale ratios and generates the reduced image G2.

Subsequently, the pattern matching is performed (Step S34: Pattern matching). Specifically, the CPU 61 performs the pattern matching with respect to the reduced image G2 generated in Step S33 and extracts the indentation area K1. Thus, the CPU 61 serves as a pattern matcher that performs the pattern matching with respect to the reduced image G2 generated by the reduced image generator and extracts the indentation area K1. Pattern matching employing a normalized correlation method is described below with reference to FIGS. 10 to 13.

Figure 10:
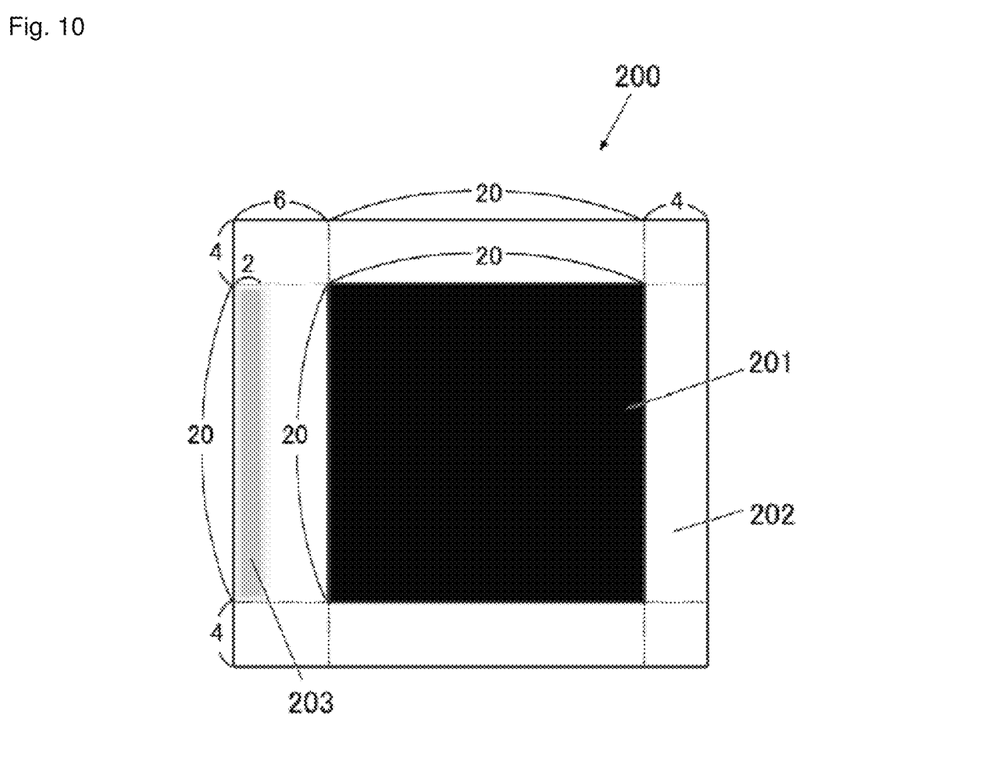
FIG. 10 illustrates an exemplary scanning model.

In the present embodiment, a scanning model 200 shown in FIG. 10 is used for the pattern matching. The scanning model 200 has a rectangular shape and has 840 pixels composed of 28 pixels in an X direction by 30 pixels in a Y direction. The scanning model 200 has a black area 201, a white area 202, and a gray area 203. The black area 201, which is provided in substantially a central portion, corresponds to an area of a known indentation shape corresponding to the indenter 14a rotated by 45°. The white area 202 surrounds the black area 201. The gray area 203 is provided in a central portion of a left end portion. The gray area 203 is not used for the pattern matching. The black area 201 includes 400 pixels composed of rows and columns of 20 pixels each. The gray area 203 includes 40 pixels composed of rows of 20 pixels and columns of 2 pixels. The white area 202 includes 400 pixels, which is a remainder of the entire area from which the black area 201 and the gray area 203 are subtracted. In other words, the black area 201 and the white area 202 include an equal number of pixels. Thus, when each pixel included in the black area 201 counts −1 and each pixel included in the white area 202 counts 1, the sum of the pixels used in the scanning model 200 equals 0.

Figure 11:
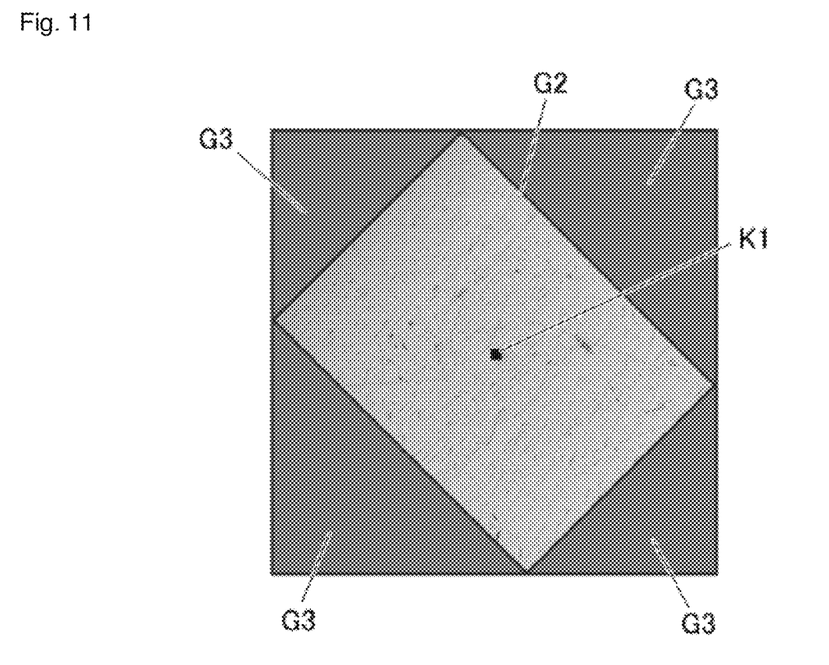
FIG. 11 illustrates an area surrounding the reduced image of FIG. 9 where no matching is performed.
Figure 12:
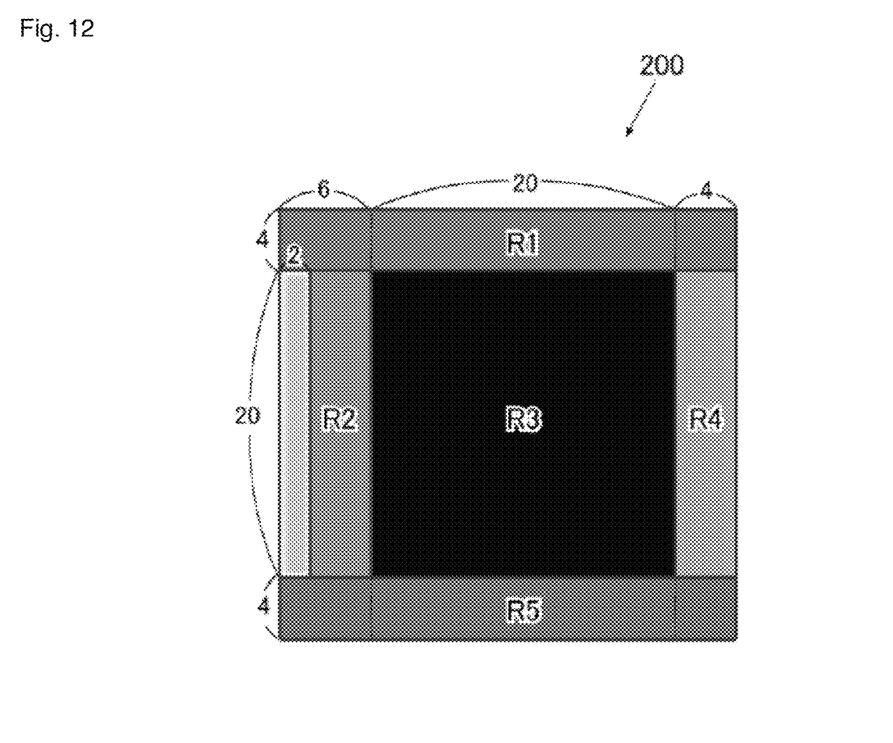
FIG. 12 illustrates an example in which the scanning model of FIG. 10 is divided into five areas.

In the present embodiment, matching is performed with the scanning model 200 by raster scanning the reduced image G2 (refer to FIG. 9) generated in Step S33. However, matching is not performed in an area G3 where no image is formed around the reduced image G2 as shown in FIG. 11. Specifically, the scanning model 200 is first divided into five areas R1 to R5 as shown in FIG. 12. The area C is assigned to the black area 201, while the remaining areas A, B, D, and E are assigned to the white area 202. A degree of correlation m can be calculated by Expression 1, where sums of luminance values of the areas R1 to R5 are A to E, respectively; sums of squares of the luminance values in the areas R1 to R5 are A2 to E2, respectively; the number of pixels of 1 (black pixel) or −1 (white pixel) is N; and a sum of A to E is K.

$$m = (A+B+D+E-C)/\mathrm{sqrt}\,(N)/\mathrm{sqrt}\,(A2+B2+C2+D2+E2-K \times K/N) \quad (1)$$

Figure 13:
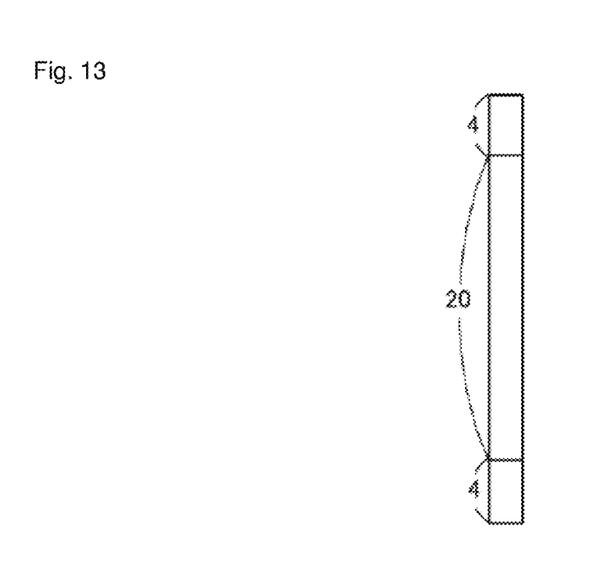
FIG. 13 illustrates an area of one column of the scanning model.

To accelerate matching in the present embodiment, six Expressions 2 to 7 below are calculated per column as shown in FIG. 13, where a sum of luminance values in an area of four rows from an upper end portion is U; a sum of luminance values in an area of four rows from a lower end portion is DN; and a sum of luminance values in an area of 20 rows in the middle is Med. In Expressions 2 to 7, "st" denotes a row start number; "st_r" denotes a column start number; and "I [x] [y]" denotes a luminance value of a coordinate (x, y).

[Formulae 1]

$$U[i] = \sum_{j=0}^{j=3} I[st+j][i] \quad (2)$$

$$U2[i] = \sum_{j=0}^{j=3} I[st+j][i] * I[st+j][i] \quad (3)$$

$$Med[i] = \sum_{j=4}^{j=23} I[st+j][i] \quad (4)$$

$$Med2[i] = \sum_{j=4}^{j=23} I[st][i] * I[st+j][i] \quad (5)$$

$$D[i] = \sum_{j=24}^{j=27} I[st+j][i] \quad (6)$$

$$DN2[i] = \sum_{j=24}^{j=27} I[st+j][i] * I[st+j][i] \quad (7)$$

After calculation of Expressions 2 to 7, A to E and A2 to E2 are calculated using values calculated from Expressions 2 to 7. For example, A and A2 can be calculated by Expressions 8 and 9, respectively. In Expressions 8 and 9, "st_r" denotes a column start number.

[Formulae 2]

$$A = \sum_{j=0}^{j=29} U[\mathrm{st\_r}+j] \quad (8)$$

$$A2 = \sum_{j=0}^{j=29} U2[\mathrm{st\_r}+j] \quad (9)$$

The remaining B to E and B2 to E2 can be calculated using values calculated from Expressions 2 to 7. Then, the calculated A to E and A2 to E2 are substituted into Expression 1 above and thus the degree of correlation m in one area of the scanning model 200 can be calculated. Thereafter, matching is performed by raster scanning in which the scanning model 200 is shifted by approximately one area in the column direction, and then the degree of correlation m is calculated. In this process, for instance, A and A2 can be calculated in Expressions 10 and 11, respectively.

$$A = A + U\,[st\_r+30] - U\,[st\_r] \quad (10)$$

$$A2 = A2 + U2\,[st\_r+30] - U2\,[st\_r] \quad (11)$$

The remaining B to E and B2 to E2 can be calculated in a similar manner to the above. Thereafter, matching is performed in a similar manner by raster scanning in which the scanning model 200 is shifted by approximately one area in the column direction, and then the degree of correlation m is calculated.

When raster scanning reaches the right-most end of the reduced image G2, the scanning model 200 is shifted by approximately one area in the row direction and is moved to the start column, specifically, the left-most end of the reduced image G2. In association with the move, Expressions 2 to 7 above are re-calculated. For example, U and U2 can be calculated by Expressions 12 and 13, respectively.

$$U\,[i] = U\,[i] + I\,[st+4][i] - I\,[st][i] \quad (12)$$

$$U2\,[i] = U2\,[i] + I\,[st+4][i] \times I\,[st+4][i] - I\,[st][i] \times I\,[st][i] \quad (13)$$

The remaining Med, Med2, DN, and DN2 can also be calculated in a similar manner to the above. Then, A to E and A2 to E2 are calculated using the re-calculated U, U2, Med, Med2, DN, and DN2, and the degree of correlation m is calculated. After the degree of correlation m is calculated in all areas in the reduced image G2, the pattern matching ends and the process proceeds to the next Step S35.

Subsequently, in Step S35 of FIG. 7, a determination is made as to whether a maximum degree of correlation is equal to or greater than a threshold value (Step S35). Specifically, the CPU 61 determines whether the maximum degree of correlation calculated in the pattern matching in Step S34 is equal to or greater than the predetermined threshold value. The predetermined threshold value may be any value, provided that the value represents correlation with the indentation area K1. When the maximum degree of correlation is determined to be equal to or greater than the threshold value (Step S35: Yes), the CPU 61 determines that the reduced image G2 generated in Step S33 includes the indentation area K1 and obtains a coordinate value showing the maximum degree of correlation and a scale ratio of the reduced image G2 (Step S36). Then, the CPU 61 extracts the indentation area K1 based on the coordinate value of the maximum degree of correlation and the scale ratio obtained in Step S36, ends the indentation area extraction of FIG. 7, and proceeds to Step S4 of FIG. 5. Meanwhile, when the maximum degree of correlation is determined to be less than the threshold value (Step S35: No), the CPU 61 proceeds to Step S32 and determines whether the pattern matching is complete for all scale ratios. Thus, the CPU 61 as the pattern matcher extracts the indentation area K1 based on the degree of correlation m calculated by scanning the reduced image G2 with the scanning model 200 that includes the indentation shape corresponding to the indenter 14a (black area 201). Furthermore, the CPU 61 as the pattern matcher calculates the degree of correlation m by scanning the reduced image G2 at the scale ratios in the predetermined sequence. When the maximum degree of correlation among the calculated degrees of correlation m is determined to be equal to or greater than the predetermined threshold value (Step S35: Yes), the CPU 61 extracts the area showing the maximum degree of correlation as the indentation area K1.

When the pattern matching is determined to be complete for all scale ratios (Step S32: Yes), the CPU 61 obtains the coordinate value of the maximum degree of correlation and the scale ratio (Step S37). Specifically, the CPU 61 determines that, among all degrees of correlation calculated in the pattern matching for all scale ratios, the reduced image G2 that includes the maximum degree of correlation includes the indentation area K1, and the CPU 61 obtains the coordinate value showing the maximum degree of correlation and the scale ratio of the reduced image G2. Then, the CPU 61 extracts the indentation area K1 based on the coordinate value of the maximum degree of correlation and the scale ratio obtained in Step S37, ends the indentation area extraction of FIG. 7, and then proceeds to Step S4 of FIG. 5. Thus, the CPU 61, which serves as the pattern matcher, extracts as the indentation area K1 the area showing the maximum degree of correlation among all degrees of correlation m calculated by scanning all reduced images G2 at all scale ratios.

Subsequently, in Step 4 of FIG. 5, indentation area analysis is performed (Step S4). Specifically, the CPU 61 executes analytical processing, including binarization, with respect to the indentation area K1 extracted in the indentation area extraction of Step S3, and then extracts a vertex for indentation measurement to measure dimensions of the indentation. A specific method of analytical processing can utilize a commonly known technology. Therefore, a detailed description thereof is omitted. Subsequently, hardness of the sample S is calculated (Step S5: Hardness calculation). Specifically, the CPU 61 measures a length of a diagonal line of the indentation with reference to a coordinate value of the vertex for indentation measurement extracted in Step S4, and then calculates the hardness of the sample S based on the measured length of the diagonal line. Thus, the CPU 61 serves as a hardness calculator that calculates the hardness of the sample S based on the indentation area K1 extracted by the indentation area extractor.

Subsequently, the hardness of the sample S is displayed (Step S6). Specifically, the CPU 61 controls the monitor 8 to display the hardness of the sample S calculated in Step S5. Thus, the CPU 61 serves as a display controller that displays on the monitor 8 the hardness of the sample S calculated by the hardness calculator.

As described above, the hardness tester 100 according to the present embodiment serves as the indentation former (CPU 61), the image capture controller (CPU 61), the indentation area extractor (CPU 61), and the hardness calculator (CPU 61). The indentation former forms the indentation in the surface of the sample S by pressing the indenter 14a against the surface of the sample S. The image capture controller controls the image capturer (CCD camera 12) to capture an image of the surface of the sample S and obtains image data of the surface of the sample S. The indentation area extractor extracts the indentation area K1 formed in the surface of the sample S based on the image data of the surface of the sample S obtained by the image capture controller. The hardness calculator calculates the hardness of the sample S based on the indentation area K1 extracted by the indentation area extractor. Furthermore, the indentation area extractor has the reduced image generator (CPU 61) and the pattern matcher (CPU 61). The reduced image generator reduces the image G1 obtained from the image data of the surface of the sample S at a scale ratio selected from the plurality of predetermined scale ratios and generates the reduced image G2. The pattern matcher performs pattern matching with respect to the reduced image G2 generated by the reduced image generator and extracts the indentation area K1. Thus, the hardness tester 100 according to the present embodiment does not need to perform binarization when extracting the indentation area K1, and is thus capable of extracting the indentation area K1 accurately without being affected by a change in luminance or a contamination. Furthermore, the pattern matching accelerates the extraction of the indentation area K1.

In particular, according to the hardness tester 100 of the present embodiment, the pattern matcher extracts the indentation area K1 based on the degree of correlation m calculated by scanning the reduced image G2 with the model including the indentation shape corresponding to the indenter 14a (scanning model 200). This allows high-speed scanning of the reduced image G2, and thus accelerates the extraction of the indentation area K1.

Furthermore, according to the hardness tester 100 of the present embodiment, the pattern matcher calculates the degrees of correlation m by scanning the reduced image G2 at the scale ratios in the predetermined sequence. When the maximum degree of correlation among the calculated degrees of correlation m is determined to be equal to or greater than the predetermined threshold value, the pattern matcher extracts the area showing the maximum degree of correlation as the indentation area K1. This allows extraction of the area that has a correlation with the indentation shape corresponding to the indenter 14a as the indentation area K1 without scanning all reduced images G2, and thus shortens the processing time.

Furthermore, according to the hardness tester 100 of the present embodiment, the pattern matcher extracts as the indentation area K1 the area showing the maximum degree of correlation among all degrees of correlation m calculated by scanning all reduced images G2 at all scale ratios. This allows extraction of the area that has the highest degree of correlation with the indentation shape corresponding to the indenter 14a, and thus achieves accurate extraction of the indentation area K1.

A concrete description was given based on the embodiment according to the present invention. However, the present invention is not limited to the above-described embodiment and may be modified within a scope not deviating from the substance of the invention.

For example, in the embodiment above, after the pattern matching (Step S34 of FIG. 7) is performed, a determination is made as to whether the calculated maximum degree of correlation is equal to or greater than a threshold value (Step S35). When the maximum degree of correlation is determined to be equal to or greater than the threshold value (Step S35: Yes), the coordinate value showing the maximum degree of correlation and the scale ratio of the reduced image G2 are obtained (Step S36). However, the present invention is not limited to this. After the pattern matching, for instance, the process may proceed to Step S32, without performing the determination of Step S35, to determine whether the pattern matching is complete for all scale ratios. In this case, among all degrees of correlation calculated in the pattern matching for all scale ratios, the reduced image G2 that includes the maximum degree of correlation is constantly determined to include the indentation area K1, and the coordinate value showing the maximum degree of correlation and the scale ratio of the reduced image G2 are obtained.

Furthermore, in the embodiment above, a normalized correlation method is employed to describe pattern matching. However, the present invention is not limited to this. For example, the normalized correlation method may be replaced by geometric matching or generalized Hough transform to perform pattern matching.

In the embodiment above, the calculated hardness of the sample S is displayed on the monitor 8 (Step S6 of FIG. 5) to notify the user of the hardness. However, the present invention is not limited to this. For example, a speaker capable of outputting audio may be provided to output audio from the speaker, instead of the display on the monitor 8. Alternatively, audio may be output from the speaker simultaneously with the display on the monitor 8.

Furthermore, in the embodiment above, a Vickers hardness tester is described to exemplify the hardness tester 100. However, the present invention is not limited to this. The present invention may be applied to any hardness tester having an indenter with a known shape. For example, the present invention may also be applied to a Knoop hardness tester having a rhomboid pyramid diamond indenter.

In addition, within a scope not deviating from the substance of the present invention, appropriate modifications may also be made to detailed structures and operations of each component configuring the hardness tester 100.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular structures, materials and embodiments, the present invention is not intended to he limited to the particulars disclosed herein; rather, the present invention extends to all functionally equivalent structures, methods and uses, such as are within the scope of the appended claims.

The present invention is not limited to the above-described embodiments, and various variations and modifications may be possible without departing from the scope of the present invention.

What is claimed is:

1. A hardness tester for measuring hardness of a sample by applying a predetermined test force to a surface of the sample with an indenter to form an indentation and measuring dimensions of the indentation, the hardness tester comprising:
a central processing unit, comprising
an indentation former configured to form the indentation in the surface of the sample by pressing the indenter against the surface of the sample;
an image capture controller configured to control an image capturer to capture an image of the surface of the sample and obtain image data of the surface of the sample;
an indentation area extractor configured to extract an indentation area formed in the surface of the sample based on the image data of the surface of the sample obtained by the image capture controller, the indentation area extractor comprising:
a reduced image generator configured to reduce the image obtained from the image data of the surface of the sample at a scale ratio selected from a plurality of predetermined scale ratios, the reduced image generator further configured to generate a reduced image; and
a pattern matcher configured to perform pattern matching with respect to the reduced image generated by the reduced image generator by comparing luminance values of the reduced image with luminance values of a scanning model and determining a degree of correlation between the reduced image and the scanning model, the pattern matcher further configured to extract the indentation area from the reduced image; and
a hardness calculator configured to calculate the hardness of the sample based on the indentation area extracted by the indentation area extractor,
wherein the degree of correlation between the reduced image and the scanning model based on the luminance values is calculated on a per column basis.

2. The hardness tester according to claim 1, wherein the pattern matcher is further configured to extract the indentation area based on a degree of correlation calculated by scanning the reduced image with the scanning model including an indentation shape corresponding to the indenter.

3. The hardness tester according to claim 2, wherein the pattern matcher is further configured to:
calculate the degrees of correlation by scanning the reduced image at the scale ratios in a predetermined sequence; and
extract an area showing the maximum degree of correlation as the indentation area when a maximum degree of correlation among the calculated degrees of correlation is determined to be equal to or greater than a predetermined threshold value.

4. The hardness tester according to claim 2, wherein the pattern matcher is further configured to extract, as the indentation area, the area showing the maximum degree of correlation among all degrees of correlation calculated by scanning all reduced images at all scale ratios.

5. The hardness tester according to claim 3, wherein the pattern matcher is further configured to extract, as the indentation area, the area showing the maximum degree of correlation among all degrees of correlation calculated by scanning all reduced images at all scale ratios.

6. The hardness tester according to claim 1, further comprising a display controller configured to display, on a display, the hardness of the sample calculated by the hardness calculator.

7. The hardness tester according to claim 2, further comprising a display controller configured to display, on a display, the hardness of the sample calculated by the hardness calculator.

8. The hardness tester according to claim 3, further comprising a display controller configured to display, on a display, the hardness of the sample calculated by the hardness calculator.

9. The hardness tester according to claim 4, further comprising a display controller configured to display, on a display, the hardness of the sample calculated by the hardness calculator.

10. The hardness tester according to claim 5, further comprising a display controller configured to display, on a display, the hardness of the sample calculated by the hardness calculator.

11. A method of testing hardness with a hardness tester by applying a predetermined test force to a surface of a sample with an indenter to form an indentation and measuring dimensions of the indentation, the method comprising:
   forming the indentation in the surface of the sample by pressing the indenter against the surface of the sample;
   controlling an image capturer to capture an image of the surface of the sample and obtain image data of the surface of the sample;
   extracting an indentation area formed in the surface of the sample based on the image data of the surface of the sample obtained in said controlling the image capturer, said extracting the indentation area comprising:
   reducing the image obtained from the image data of the surface of the sample at a scale ratio selected from a plurality of predetermined scale ratios, and generating a reduced image;
   performing pattern matching with respect to the reduced image generated in said reducing the image by comparing luminance values of the reduced image with luminance values of a scanning model and determining a degree of correlation between the reduced image and the scanning model; and
   extracting the indentation area from the reduced image; and
   calculating the hardness of the sample based on the indentation area extracted in said extracting an indentation area,
   wherein the degree of correlation between the reduced image and the scanning model based on the luminance values is calculated on a per column basis.

12. The hardness tester according to claim 1, wherein the scanning model is divided into a plurality of portions having different luminance values.

13. The hardness tester according to claim 12, wherein one portion of the plurality of portions included in the scanning model corresponds to the indentation area.

14. The hardness tester according to claim 12, wherein the portions in the scanning model have rectangular shapes.

15. The hardness tester according to claim 12, wherein the degree of correlation between the reduce image and the scanning model is determined with respect to one portion of the scanning model at a time.

16. The hardness tester according to claim 1, wherein the reduced image is rotated prior to performing the pattern matching.

17. The hardness tester according to claim 1, further comprising:
   determining measurements of the extracted indentation area for calculating the hardness of the sample.

18. The hardness tester according to claim 1, wherein the pattern matching is performed by raster scanning in which the scanning model is shifted in a column direction to calculate the degree of correlation.

* * * * *